(12) United States Patent
Hong et al.

(10) Patent No.: US 11,793,755 B2
(45) Date of Patent: *Oct. 24, 2023

(54) PHARMACEUTICAL COMPOSITION FOR INTRAARTICULAR DELIVERY

(71) Applicants: TAIWAN LIPOSOME CO., LTD., Taipei (TW); TLC BIOPHARMACEUTICALS, INC., South San Francisco, CA (US)

(72) Inventors: Keelung Hong, South San Francisco, CA (US); Luke S. S. Guo, South San Francisco, CA (US); Yun-Long Tseng, Taipei (TW); Sheue-Fang Shih, Taipei (TW); Po-Chun Chang, Taipei (TW); Chih-Chiang Tsai, Taipei (TW); Hong-Hui Lin, Taipei (TW)

(73) Assignees: TAIWAN LIPOSOME CO., LTD., Taipei (TW); TLC BIOPHARMACEUTICALS, INC., South San Francisco, CA (US)

( * ) Notice: Subject to any disclaimer, the term of this patent is extended or adjusted under 35 U.S.C. 154(b) by 109 days.

This patent is subject to a terminal disclaimer.

(21) Appl. No.: 17/141,550

(22) Filed: Jan. 5, 2021

(65) Prior Publication Data
US 2021/0145744 A1 May 20, 2021

Related U.S. Application Data

(63) Continuation of application No. 16/875,167, filed on May 15, 2020, now Pat. No. 10,959,951, which is a continuation of application No. 16/439,124, filed on Jun. 12, 2019, now Pat. No. 10,736,846, which is a continuation of application No. 15/695,649, filed on Sep. 5, 2017, now Pat. No. 10,322,086, which is a continuation of application No. 14/411,530, filed as application No. PCT/US2013/049442 on Jul. 5, 2013, now Pat. No. 9,789,062.

(60) Provisional application No. 61/791,650, filed on Mar. 15, 2013, provisional application No. 61/668,446, filed on Jul. 5, 2012.

(51) Int. Cl.
| | | |
|---|---|---|
| A61K 9/127 | (2006.01) | |
| A61K 31/405 | (2006.01) | |
| A61K 31/519 | (2006.01) | |
| A61K 31/573 | (2006.01) | |
| A61K 38/17 | (2006.01) | |
| A61K 9/00 | (2006.01) | |
| A61K 9/19 | (2006.01) | |
| A61K 47/24 | (2006.01) | |
| A61K 47/28 | (2006.01) | |

(52) U.S. Cl.
CPC ............ *A61K 9/127* (2013.01); *A61K 9/0019* (2013.01); *A61K 9/19* (2013.01); *A61K 31/405* (2013.01); *A61K 31/519* (2013.01); *A61K 31/573* (2013.01); *A61K 38/1793* (2013.01); *A61K 47/24* (2013.01); *A61K 47/28* (2013.01); *C07K 2319/30* (2013.01)

(58) Field of Classification Search
CPC ........ A61K 9/127; A61K 9/0019; A61K 9/19; A61K 31/405; A61K 31/519; A61K 31/573; A61K 38/1793; A61K 47/24; C07K 2319/30
See application file for complete search history.

(56) References Cited

U.S. PATENT DOCUMENTS

| | | | | | |
|---|---|---|---|---|---|
| 5,366,958 | A | * | 11/1994 | Weiner | A61K 47/62 530/812 |
| 5,846,217 | A | * | 12/1998 | Beck | A61N 1/0448 604/20 |
| 2002/0010180 | A1 | * | 1/2002 | Feldmann | A61K 38/1793 514/250 |
| 2005/0260260 | A1 | * | 11/2005 | Kisak | A61K 9/1271 424/450 |
| 2010/0227807 | A1 | * | 9/2010 | Stossel | A61P 11/06 435/29 |
| 2011/0033468 | A1 | * | 2/2011 | Shih | A61K 31/7088 424/139.1 |

* cited by examiner

*Primary Examiner* — Snigdha Maewall
(74) *Attorney, Agent, or Firm* — Leason Ellis LLP

(57) ABSTRACT

The present invention provides methods of treating arthritis. A sustained release composition comprising liposomes and one or more therapeutic agent or a pharmaceutically acceptable salt thereof is administered to a subject in need thereof. The liposomes may be in an aqueous suspension. The sustained release composition can be administered intraarticularly.

21 Claims, 11 Drawing Sheets

(a)

(b)

PHARMACEUTICAL COMPOSITION FOR INTRAARTICULAR DELIVERY

CROSS-REFERENCE TO RELATED APPLICATIONS

This application is a continuation application of U.S. patent application Ser. No. 16/875,167, filed on May 15, 2020, which is a continuation application of U.S. patent application Ser. No. 16/439,124, filed on Jun. 12, 2019, now U.S. Pat. No. 10,736,846, which is a continuation of U.S. patent application Ser. No. 15/695,649, filed on Sep. 5, 2017, now U.S. Pat. No. 10,322,086, which is a continuation of U.S. patent application Ser. No. 14/411,530, filed on Dec. 29, 2014, now U.S. Pat. No. 9,789,062, which is a national stage under 35 U.S.C. 371 of International Application PCT/US2013/049442, filed on Jul. 5, 2013, which claims the benefit of priority from U.S. Provisional Patent Application No. 61/668,446, filed on Jul. 5, 2012 and U.S. Provisional Patent Application No. 61/791,650, filed on Mar. 15, 2013, the entire contents of each of which are incorporated herein by reference.

BACKGROUND OF THE INVENTION

Osteoarthritis (OA) is the most common type of arthritis and a leading cause of disability. It is a non-inflammatory, degenerative joint disease characterized by progressive loss of articular cartilage, subchondral bone sclerosis, osteophyte formation, changes in the synovial membrane, and an increased volume of synovial fluid with reduced viscosity and hence changed lubrication properties.

Rheumatoid arthritis (RA) is a chronic systemic inflammatory disease of unknown cause. Genetic, environmental, hormonal, immunologic, and infectious factors can play significant roles. The hallmark feature of this condition is persistent symmetric polyarthritis that affects the hands and feet, although any joint lined by a synovial membrane can be involved. This is due to the accumulation of and proliferation of inflammatory cells in the synovial lining, known as synovitis. Extra-articular involvement of organs such as the skin, heart, lungs, and eyes can be significant.

Intraarticular (IA) drug injection is an attractive treatment approach for treatment of arthritis, including OA and RA. The various steroid and hyaluronic acid formulations on the market are considered effective, but require frequent IA injections and provide only short-term symptomatic relief. Other crystal suspension formulations, which require large bore needles for IA injection are not suitable for treating small joints and can produce a crystal-induced synovitis. The available systemic treatments also have shortcomings, most notably side effects.

In view of the deficiencies outlined above, there is a need for methods for treating arthritis with less frequent IA injection and/or longer-term pain relief. The methods disclosed herein address this need as well as other important needs.

BRIEF SUMMARY OF THE INVENTION

The terms "invention," "the invention," "this invention" and "the present invention" used herein are intended to refer broadly to all of the subject matter of this patent application and the claims below. Statements containing these terms should be understood not to limit the subject matter described herein or to limit the meaning or scope of the patent claims below. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim.

The present invention is directed to methods of treating arthritis, comprising intraarticularly injecting into a subject in need of such treatment a sustained release composition, whereby the arthritis symptoms in the subject are reduced. The present invention is particularly useful for treating rheumatoid arthritis.

The sustained release composition of the present invention comprises liposomes comprising (a) a phospholipid or a mixture of phospholipids, and cholesterol; and (b) a therapeutic agent or a pharmaceutically acceptable salt thereof, wherein the liposomes are in an aqueous suspension. The sustained release composition can be prepared by mixing a lipid cake with a therapeutic agent.

DETAILED DESCRIPTION OF THE INVENTION

Figure 1:
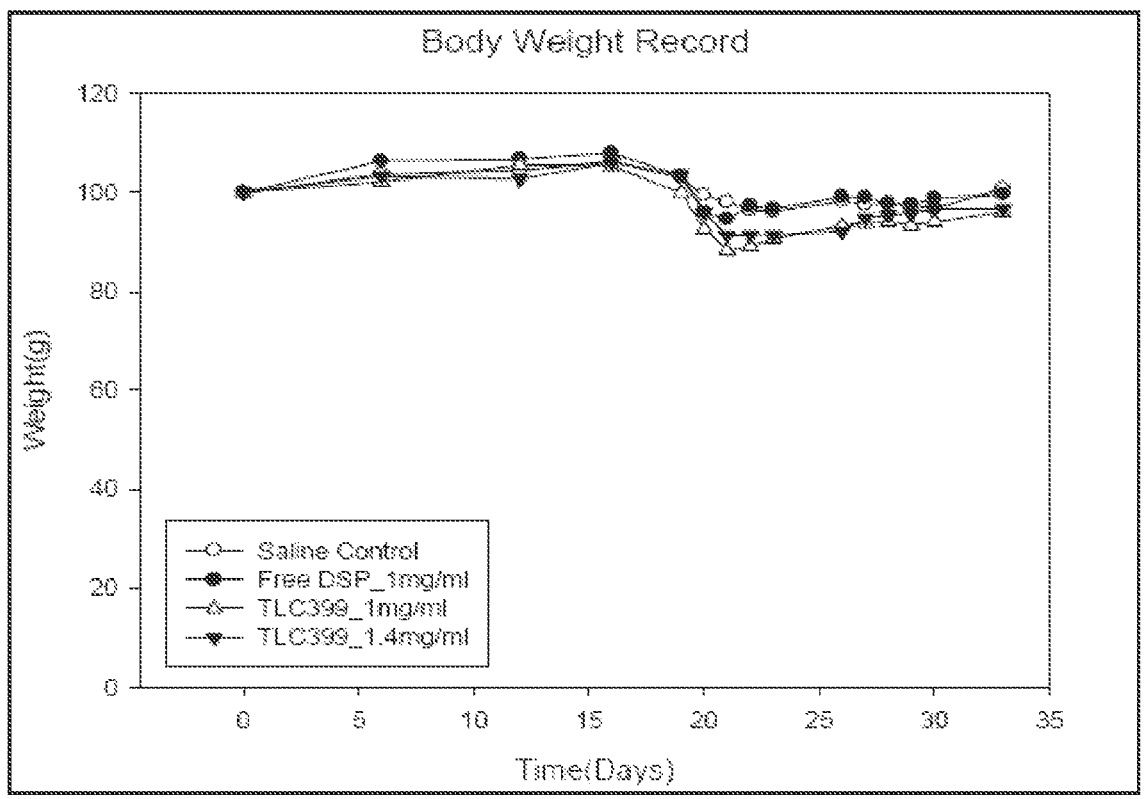
FIG. 1 is a line plot showing the changes in body weight in 4 groups of rats after each group was subjected, respectively, to a single IA injection of saline, free dexamethasone sodium phosphate (DSP) or the sustained release compositions.

As disclosed herein, it was discovered that IA administration to a subject of an effective amount of a sustained release composition described herein, can advantageously reduce signs and/or symptoms of arthritis in the subject. It was also discovered that the arthritis treatments disclosed herein can require less frequent IA injections than previously known treatments. Also discovered was that the arthritis treatments disclosed herein lead to longer-term pain relief than previously known treatments. These discoveries are embodied in the methods, compositions and medicaments for treating arthritis, described herein, as well as in the uses of the compositions for treating arthritis.

Definitions

As employed above and throughout the disclosure, the following terms, unless otherwise indicated, shall be understood to have the following meanings.

As used herein, the singular forms "a," "an," and "the" include the plural reference unless the context clearly indicates otherwise.

The term "liposome," "liposomes" and the related terms, as used herein, include multivesicular liposome (MVL), multi-lammellar vesicles (MLU) or small or large unilammellar vesicles (ULV). The liposomes are nano-sized and comprise a particle-forming component and an agent-carrying component. The particle-forming component forms an enclosed lipid barrier, substantially free of neutral lipid such as triglyceride. In certain embodiments, there is less than about 0.1% of neutral lipid in the particle-forming component. In other embodiments, there is no neutral lipid in the particle-forming component. The agent carrying component comprises a substantially aqueous medium, substantially free of neutral lipid, such as triglyceride, non-aqueous phase (oil phase), water-oil emulsions or other mixtures containing non-aqueous phase.

The term "effective amount," as used herein, refers to a dose of the sustained release composition that is sufficient to reduce the symptoms and/or signs of arthritis, such as pain and joint stiffness.

The term "treating," "treated," or "treatment" as used herein includes preventative (e.g. prophylactic), palliative, and curative methods, uses or results. The terms "treatment" or "treatments" can also refer to compositions, such as pharmaceutical compositions, or medicaments.

Throughout this application, by treating is meant a method of reducing or delaying one or more effects or symptoms of arthritis. Treatment can also refer to a method of reducing the underlying pathology rather than just the symptoms. The treatment can be any reduction and can be, but is not limited to, the complete ablation of arthritis, signs or symptoms of arthritis. Treatment can include the complete amelioration of arthritis as detected by art-known techniques. Art recognized methods are available to detect arthritis and its symptoms. These include, but are not limited to, radiological examination, joint aspiration, blood tests (for example, detection of rheumatoid factors or an anti-CCP test) or MRI, to name a few. For example, a disclosed method is considered to be a treatment if there is about a 10% reduction in one or more symptoms of arthritis in a subject when compared to the subject prior to treatment or control subjects. Thus, the reduction can be about a 10, 20, 30, 40, 50, 60, 70, 80, 90, 100%, or any amount of reduction in between.

As utilized herein, by prevent, preventing, or prevention is meant a method of precluding, delaying, averting, obviating, forestalling, stopping, or hindering the onset, incidence, severity, or recurrence of arthritis. For example, the disclosed method is considered to be a prevention if there is a reduction or delay in onset, incidence, severity, or recurrence of arthritis or one or more symptoms of arthritis (for example, pain, stiffness, fever, joint inflammation or joint tenderness) in a subject susceptible to arthritis as compared to control subjects susceptible to arthritis that did not receive a treatment disclosed herein. The disclosed method is also considered to be a prevention if there is a reduction or delay in onset, incidence, severity, or recurrence of arthritis or one or more symptoms of arthritis in a subject susceptible to arthritis after receiving a treatment disclosed herein as compared to the subject's progression prior to receiving treatment. Thus, the reduction or delay in onset, incidence, severity, or recurrence of arthritis can be about a 10, 20, 30, 40, 50, 60, 70, 80, 90, 100%, or any amount of reduction in between.

The term "subject" can refer to a vertebrate having arthritis or to a vertebrate deemed to be in need of arthritis treatment. Subjects include warm-blooded animals, such as mammals, such as a primate, and, more preferably, a human Non-human primates are subjects as well. The term subject includes domesticated animals, such as cats, dogs, etc., livestock (for example, cattle, horses, pigs, sheep, goats, etc.) and laboratory animals (for example, mouse, rabbit, rat, gerbil guinea pig, etc.). Thus, veterinary uses and medical formulations are contemplated herein. The term "arthritis" refers to a joint disorder or condition that involves inflammation of one or more joints. The term "arthritis," as used herein, encompasses a variety of types and subtypes of arthritis of various etiologies and causes, either known or unknown, including, but not limited to, rheumatoid arthritis, osteoarthritis, infectious arthritis, psoriatic arthritis, gouty arthritis, and lupus-related arthritis.

Lipid Cake

A lipid cake used in the arthritis treatments described herein contains a solid lipid mixture in a cake, film or powder form.

In certain embodiments, the phospholipid and cholesterol, or mixture of phospholipids and cholesterol are pre-formed into liposomes before further processing into a lipid cake.

In certain embodiments, the phospholipid and cholesterol, or mixture of phospholipids and cholesterol are not pre-formed into liposomes before further processing into a lipid cake.

A lipid cake can be prepared from a variety of lipids capable of either forming or being incorporated into a unilayer or bilayer structure. The lipid cakes provided herein include one or more phospholipids and cholesterol, substantially free of neutral lipid such as triglyceride. Examples of the phospholipids include, but are not limited to, phosphatidylcholine (PC), phosphatidylglycerol (PG), phosphatidylethanolamine (PE), phosphatidylserine (PS), phosphatidic acid (PA), phosphatidylinositol (PI), egg phosphatidylcholine (EPC), egg phosphatidylglycerol (EPG), egg phosphatidylethanolamine (EPE), egg phosphatidylserine (EPS), egg phosphatidic acid (EPA), egg phosphatidylinositol (EPI), soy phosphatidylcholine (SPC), soy phosphatidylglycerol (SPG), soy phosphatidylethanolamine (SPE), soy phosphatidylserine (SPS), soy phosphatidic acid (SPA), soy phosphatidylinositol (SPI), dipalmitoylphosphatidylcholine (DPPC), 1,2-dioleoyl-sn-glycero-3-phosphatidylcholine (DOPC), dimyristoylphosphatidylcholine (DMPC), dipalmitoylphosphatidylglycerol (DPPG), dioleoylphosphatidylglycerol (DOPG), dimyristoylphosphatidylglycerol (DMPG), hexadecylphosphocholine (HEPC), hydrogenated soy phosphatidylcholine (HSPC), distearoylphosphatidylcholine (DSPC), distearoylphosphatidylglycerol (DSPG), dioleoylphosphatidylethanolamine (DOPE), palmitoylstearoylphosphatidylcholine (PSPC), palmitoylstearoylphosphatidylglycerol (PSPG), monooleoylphosphatidylethanolamine (MOPE), 1-palmitoyl-2-oleoyl-sn-glycero-3-phosphatidylcholine (POPC), polyethyleneglycol distearoylphosphatidylethanolamine (PEG-DSPE), dipalmitoylphosphatidylserine (DPPS), 1,2-dioleoyl-sn-glycero-3-phosphatidylserine (DOPS), dimyristoylphosphatidylserine (DMPS), distearoylphosphatidylserine (DSPS), dipalmitoylphosphatidic acid (DPPA), 1,2-dioleoyl-sn-glycero-3-phosphatidic acid (DOPA), dimyristoylphosphatidic acid (DMPA), distearoylphosphatidic acid (DSPA), dipalmitoylphosphatidylinositol (DPPI), 1,2-dioleoyl-sn-glycero-3-phosphatidylinositol (DOPI), dimyristoylphosphatidylinositol (DMPI), distearoylphosphatidylinositol (DSPI). Lipids can be mixtures of one or more of the foregoing lipids, or mixtures of one or more of the foregoing lipids with one or more other lipids not listed above.

In an exemplary embodiment, a lipid cake comprises a mixture of two phospholipids, such as DOPC or DOPG. In another embodiment, the lipid cake comprises a mixture of phospholipids selected from the group consisting of DOPC, POPC, SPC, EPC, PEG-DSPE and DOPG and cholesterol. In another embodiment, the lipid cake comprises a mixture of a first phospholipid and a second phospholipid, the first phospholipid being DOPC, POPC, SPC, or EPC and the second phospholipid being PEG-DSPE or DOPG. Various exemplary compositions of the lipid cake are disclosed in U.S. application Ser. No. 12/538,435, the teachings of which are incorporated herein by reference in their entirety.

In an exemplary embodiment, the lipid cake mixture comprises DOPC, DOPG and cholesterol at a molar ratio of about 29.5% to 90%:3% to 37.5%:10% to 33%. In another embodiment, the ratio of DOPC:DOPG:cholesterol is about 56.25-72.5:7.5-18.75:20-25 by mole percent. For example, and not to be limiting, the ratio of DOPC:DOPG:cholesterol can be about 67.5:7.5:25. In another embodiment, the lipid cake mixture comprises about 12 mole % to less than about 30 mole % of cholesterol relative to the lipid cake. In another embodiment, the lipid cake mixture comprises about 15 mole % to about 29 mole % of cholesterol relative to the lipid cake. In yet another embodiment, the lipid cake mixture comprises about 17.5 mole percent to about 28 mole % of cholesterol relative to the lipid cake.

In another embodiment, the particle-forming component is free of fatty acid or cationic lipid (i.e. a lipid carrying a net positive charge at physiological pH).

In another embodiment, the particle-forming component includes a hydrophilic polymer with a long chain of highly hydrated flexible neutral polymer attached to a phospholipid molecule. Without being bound by any theory, the hydrophilic polymer is believed to stabilize the liposome and result in a longer circulation time in vivo. Examples of the hydrophilic polymer include, but are not limited to, polyethylene glycol (PEG) with a molecular weight of about 2,000 to about 5,000 daltons, methoxy PEG (mPEG), ganglioside $GM_1$, polysialic acid, polylactic (also termed polylactide), polyglycolic acid (also termed polyglycolide), apolylacticpolyglycolic acid, polyvinyl alcohol, polyvinylpyrrolidone, polymethoxazoline, polyethyloxazoline, polyhydroxyethyloxazoline, polyhydroxypropyloxazoline, polyaspartamide, polyhydroxypropyl methacrylamide, polymethacrylamide, polydimethylacrylamide, polyvinylmethylether, polyhydroxyethyl acrylate, derivatized celluloses such as hydroxymethylcellulose or hydroxyethylcellulose and synthetic polymers.

The particle-forming component may further comprise a lipid-conjugate of an antibody or a peptide that acts as a targeting moiety to enable the liposome to specifically bind to a target cell bearing a target molecule. Examples of the target molecules include, but are not limited to, epidermal growth factor receptor (EGFR), vascular endothelial growth factor receptor (VEGF), carcinoembryonic antigen (CEA), and erbB-2/neu (HER2).

The liposomes used in the arthritis treatments described herein can be generated by conventional techniques used to prepare vesicles. These techniques include the ether injection method (Deamer et al., Acad. Sci. (1978) 308: 250), the surfactant method (Brunner et al., Biochim Biophys. Acta (1976) 455: 322), the freeze-thaw method (Pick et al., Arch. Biochim Biophys. (1981) 212: 186), the reverse-phase evaporation method (Szoka et al., Biochim Biophys. Acta. (1980) 601: 559 71), the ultrasonic treatment method (Huang et al., Biochemistry (1969) 8: 344), the ethanol injection method (Kremer et al., Biochemistry (1977) 16: 3932), the extrusion method (Hope et al., Biochim. Biophys. Acta (1985) 812:55 65), the French press method (Barenholz et al., FEBS Lett. (1979) 99: 210) and methods detailed in Szoka, F., Jr., et al., Ann. Rev. Biophys. Bioeng. 9:467 (1980). All of the references set forth above describe the processes and conventional technologies for the formation of liposome vesicles, and the descriptions of these processes are incorporated by reference herein.

In an exemplary embodiment, the therapeutic agent is encapsulated in the agent carrying component of the liposome, wherein the agent carrying component comprises a substantially aqueous medium, substantially free of neutral lipid, such as triglyceride, a non-aqueous phase (oil phase), water-oil emulsions or other mixtures containing a non-aqueous phase. An agent carrying component comprising a substantially aqueous medium provides longer therapeutic efficacy and a prolonged release profile of the therapeutic agent in the joint. In contrast, a therapeutic agent encapsulated in an agent carrying component comprising substantially non-aqueous medium (e.g. soy bean oil medium) has a more rapid release profile and shorter therapeutic efficacy. (Bias et al, Sustained-Release Dexamethasone Palmitate— Pharmacokinetics and Efficacy in Patients with Activated Inflammatory Osteoarthritis of the Knee. Clin Drug Invest 2001; 21(6):429-436.)

In certain embodiments, a lipid cake comprises one or more lipids that are not pre-formed into liposomes. The lipid cake can be prepared by dissolving the lipids in a suitable organic solvent, including, but not limited to, ethanol, methanol, t-butyl alcohol, ether and chloroform, and drying by heating, vacuum evaporation, nitrogen evaporation, lyophilization, or other conventional means of solvent removal.

After sterilization, the lipid solution is mixed with the therapeutic agent and lyophilized to form a powder or a cake. Generally, at least one cryoprotectant and at least one buffer are added to effectively lyophilize the steroid-lipid mixture.

The cryoprotectants include, but are not limited to, mannitol, glycerol, dextrose, sucrose, and/or trehalose. One exemplary cryoprotectant is mannitol.

The buffers include, but are not limited to, sodium phosphate monobasic dihydrate and sodium phosphate dibasic anhydrous.

Some examples of lipid cake preparation are described below to illustrate the processes of lipid cake preparation as they relate to the present invention.

Therapeutic Agent

A therapeutic agent can be a steroid solution, a nonsteroidal anti-inflammatory drug (NSAID) such as indomethacin, a disease-modifying anti-rheumatic drug (DMARD) or a combination of two or more of the foregoing, as well as a combination of one or more of the foregoing with other ingredients or compounds not specifically listed herein. DMARDs include small molecule agents, such as methotrexate, leflunomide, sulfasalazine, cyclophosphamide, azathioprine, cyclosporin A, d-penicillamine, antimalarial drugs (e.g. hydroxychloroquine). DMARDs also include biological substances, such as a Tumor necrosis factor α (TNF-α) antagonist (e.g. Etanercept, trade name Enbrel, commercially available from Wyeth Pharmaceuticals, Inc., Collegeville, USA, Adalimumab, trade name HUMIRA, commercially available from Abbott Laboratories, Abbott Park, Ill., USA), interleukin-1 receptor antagonist, interleukin-6 receptor antagonist, anti-CD20 monoclonal antibody, CTLA-4-Ig, RGD peptide and the like.

In an exemplary embodiment, the therapeutic agent is a substantially water soluble steroid solution, such as DSP. In another exemplary embodiment, the therapeutic agent is a substantially water soluble NSAID, such as a pharmaceutically acceptable salt of indomethacin. In yet another exemplary embodiment, the therapeutic agent is a substantially water soluble DMARD, such as a pharmaceutically acceptable salt of methotrexate, or a TNF-α antagonist. In yet another exemplary embodiment, the therapeutic agent is not covalently bound to a phospholipid or a fatty acid, such as palmitate.

A therapeutic agent or agents can be combined with pharmaceutically acceptable excipients and other ingredients suitable for pharmaceutical formulations (which include formulations for human and animal use, and formulations for research, experimental and related uses). In some embodiments, a citrate buffer is used, preferably sodium citrate. In other embodiments, a chelating agent is used, preferably EDTA.

Water soluble steroids include any naturally occurring steroid hormones, synthetic steroids and their derivatives. Water soluble steroids include, but are not limited to, cortisone, hydrocortisone, prednisolone, methylprednisolone, prednisone, dexamethasone sodium phosphate (DSP), hydrocortisone-17-valerate, fluorocortisone, fludrocortisone, methylprednisolone, paramethasone and eplerenone. In one example, and not to be limiting, a water soluble steroid is DSP. For instance, about 2 to about 100 mg/mL of DSP solution can be used to reconstitute the lipid cake.

Pharmaceutically acceptable salts of water soluble steroids include non-toxic salts formed from non-toxic inorganic or organic bases. For example, non-toxic salts can be formed with inorganic bases, such as an alkali or alkaline earth metal hydroxide, e.g., potassium, sodium, lithium, calcium, or magnesium, or with organic bases, such as an amine and the like.

Pharmaceutically acceptable salts of water soluble steroids also include non-toxic salts formed from non-toxic inorganic or organic acids. Examples of organic and inorganic acids arehydrochloric, sulfuric, phosphoric, acetic, succinic, citric, lactic, maleic, fumaric, palmitic, cholic, pamoic, mucic, D-glutamic, glutaric, glycolic, phthalic, tartaric, lauric, stearic, salicylic, sorbic, benzoic acids and the like.

Sustained Release Composition

Sustained release compositions employed in the arthritis treatments described herein are substantially free of crystal suspension. In an exemplary embodiment, there is less than about 0.1% of crystal suspension in the sustained release composition. In another embodiment, there is no crystal suspension in the sustained release composition. The sustained release compositions set forth herein comprise liposomes, wherein the liposomes comprise a phospholipid or mixture of phospholipids, cholesterol, and one or more therapeutic agents, and wherein the liposomes are in an aqueous suspension. The sustained release composition can be prepared by reconstituting a lyophilized lipid cake comprising one or more phospholipids, and cholesterol with an aqueous solution comprising one or more therapeutic agents to form an aqueous suspension. The sustained release composition can also be prepared by reconstituting a lyophilized combination of one or more therapeutic agents and a lipid cake comprising one or more phospholipids, and cholesterol with an aqueous solution to form an aqueous suspension. In some exemplary embodiments, the lipid cake consists essentially of one or more phospholipids and cholesterol as the lipid components. Suitable aqueous solutions or media for reconstitution include, but are not limited to, buffers, distilled water, saline, a sugar solution, for example, a dextrose solution, and the like. In other exemplary embodiments, the lipid cake consists essentially of a phosphatidylcholine lipid, a phosphatidylglycerol lipid and cholesterol. In yet other exemplary embodiments, the lipid cake can contain (in addition to the phosphatidylcholine, phosphatidylglycerol, and cholesterol lipids) a preservative, a cryoprotectant or combination thereof. Further provided herein are sustained release compositions comprising liposomes wherein the liposomes comprise a phospholipid or mixture of phospholipids, cholesterol, and a TNF-alpha antagonist, for example, etanercept or adalimumab, and wherein the liposomes are in an aqueous suspension. The lyophilized form of this composition is also contemplated herein.

In some embodiments, the sustained release composition further comprises at least one pharmaceutically acceptable excipient, diluent, vehicle, carrier, medium for the active ingredient, a preservative, cryoprotectant or a combination thereof.

In an exemplary embodiment, the sustained release composition of the present invention is prepared by making the lipid cake and reconstituting it with the therapeutic agent to form an aqueous suspension.

In another embodiment, the sustained release composition of the present invention is prepared by adding the therapeutic agent in the lipid mixture during the preparation of the lipid cake, followed by lyophilizing the combination of the lipid mixture and the therapeutic agent with one or more cryoprotectants to form a powder.

In an exemplary embodiment, the sustained release composition comprises a water soluble steroid with a potency equivalent to about a 2 mg dose to about a 8 mg dose of dexamethasone. For example, the potency of 4 mg DSP in the sustained release composition is equivalent to the potency of 3 mg dexamethasone. The potency of 10 mg of DSP in the sustained release composition is equivalent to the potency of 7.6 mg dexamethasone. Similarly, the potency of 40 mg methylprednisolone acetate is equivalent to the potency of 7.5 mg dexamethasone.

The sustained release compositions described herein can be used to treat a subject suffering from arthritis, such as rheumatoid arthritis.

In an exemplary embodiment, about 50% to about 95% of the therapeutic agent in the sustained release composition is in non-associated form (i.e. about 5% to about 50% of the therapeutic agent is in associated form). In another embodiment, about 60-90% of the therapeutic agent in the sustained release composition is in non-associated form. The term "therapeutic agent in non-associated form" refers to the therapeutic molecules separable via gel filtration from the phospholipid/cholesterol fraction of the sustained release composition.

In another embodiment, the weight ratio of the phospholipid and cholesterol in combination to the therapeutic agent is about 5-80 to about 1. In yet another embodiment, the weight ratio of the phospholipid and cholesterol in combination to the therapeutic agent is 5-40 to 1. For example, the weight ratio of the phospholipid and cholesterol in combination to the therapeutic agent can be about 5, 10, 15, 20, 25, 30, 35, 40, 45, 50, 55, 60, 65, 70, 75 or 80 to about 1.

Methods of Treating Arthritis

The invention is directed to methods of treating arthritis in a subject, which comprise the administration of an effective amount of the sustained release composition as described herein to a subject in need thereof, whereby the symptoms and/or signs of the arthritis in the subject are reduced.

The sustained release composition is formulated to be suitable for IA, intramuscular or subcutaneous administration. Intra-articular injection involves the following steps: 1) Identifying and marking an appropriate injection site of the joint to be treated; 2) Sterilizing the injection site using aseptic technique and optionally providing local anesthetic. 3) Inserting the needle at the injection site into the joint space. The needle insertion can optionally be performed under ultrasound guidance. A small amount of synovial fluid is aspirated to confirm that the tip of the needle is within the joint space. 4) Injecting the medication into the joint space.

The dosage of the sustained release composition of the present invention can be determined by the skilled person in the art according to the embodiments. Unit doses or multiple dose forms are contemplated, each offering advantages in certain clinical settings. According to the present invention, the actual amount of the sustained release composition to be administered can vary in accordance with the age, weight, condition of the subject to be treated, the type of joint and depends on the discretion of medical professionals.

The dose of DSP for an IA injection depends on the condition of the patient and the size of the joint. In an exemplary embodiment, the dose of DPS is about 0.2 mg to about 6 mg per IA injection. In another exemplary embodiment, the dose of DPS is about 2 to about 4 mg per IA injection for a large joint, such as a knee joint. In yet another exemplary embodiment, the dose of DSP is about 0.8 to about 1 mg per IA injection for a small joint, such as the interphalangeal joint.

In an exemplary embodiment, the dose of indomethacin per IA injection is about 5 mg to about 30 mg. In another exemplary embodiment, the dose of indomethacin per IA injection is about 10 to about 25 mg. In yet another exemplary embodiment, the dose of indomethacin per IA injection is about 15 to about 20 mg.

In an exemplary embodiment, the dose of methotrexate per IA injection is about 1 mg to about 15 mg. In another exemplary embodiment, the dose of methotrexate per IA injection is about 5 mg to about 12.5 mg. In yet another exemplary embodiment, the dose of methotrexate per IA injection is about 7.5 mg to about 10 mg.

The frequency of the IA injection ranges from daily, once every three to five days, weekly or once every two to three weeks.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention. During the studies described in the following examples, conventional procedures were followed, unless otherwise stated. Some of the procedures are described below for illustrative purpose. Publications cited herein and the material for which they are cited are hereby specifically incorporated by reference in their entireties. A number of embodiments have been described. Nevertheless, it will be understood that various modifications may be made. Accordingly, other embodiments are within the scope of the following claims.

EXAMPLES

Example 1: Preparation of a Lipid Cake

A lipid cake was prepared by the solvent injection method. The lipids, including DOPC, DOPG and cholesterol, were combined at a mole ratio of 67.5:7.5:25 and dissolved in 99.9% ethanol at about 40° C. in a flask. A tabletop ultrasonic bath was used for lipid dissolution.

The dissolved lipid solution was added to the 1.0 mM sodium phosphate solution at 100 mL/min by a peristaltic pump, and the two solutions were mixed. The lipid mixture was then passed 6-10 times through a polycarbonate membrane with a pore size of 0.2 µm. Liposomes (or large multilamellar vesicles (MLVs)) were formed and the average vesicle diameter was about 120-140 nm (measured by Malvern ZetaSizer Nano ZS-90, Malvern Instruments Ltd, Worcestershire, UK).

The liposome mixture was dialyzed and concentrated by a tangential flow filtration system with Millipore Pellicon 2 Mini Ultrafiltration Module Biomax-100C (0.1 m$^2$) (Millipore Corporation, Billerica, Mass., USA) and then sterilized using a 0.2 µm sterile filter.

The lipid concentration of the filtered liposome mixture was quantified by phosphorous assay and the liposome mixture was formulated with cryoprotectent, 2% mannitol and then sterilized again using a 0.2 µm sterile filter. The sterilized liposome mixture was then filled aseptically into vials for lyophilization.

Example 2: Preparation of a DSP Sustained Release Composition

A sustained release composition was prepared by mixing the liposome mixture described in Example 1 with a DSP solution, which comprises DSP (13.2 mg/ml) and sodium citrate (4 mg/ml), followed by lyophilization.

The lyophilized DSP-liposome cake was reconstituted with 300 µl of saline, wherein the concentration of DSP was 6.6 mg/ml. The lyophilized DSP-liposome cake was further diluted with normal saline to form the sustained release compositions as shown in Table 1, wherein the concentration of DSP was 1 mg/ml in sustained release composition 1 and 1.4 mg/ml in sustained release composition 2.

TABLE 1

Composition of the Sustained Release Compositions

| DOPC | DOPG | cholesterol | mannitol | DSP |
|---|---|---|---|---|
| Sustained Released Composition 1 (mg/ml) | | | | |
| 10.6 | 1.2 | 2.0 | 4.3 | 1 |
| Sustained Released Composition 2 (mg/ml) | | | | |
| 14.8 | 1.7 | 2.7 | 6.0 | 1.4 |

Example 3: A Single Injection of Sustained Release Compositions for Treating Arthritis An in vivo evaluation of the effect of the sustained release composition on arthritis was performed using Lewis rats. Sixteen female rats, aged 8 weeks, were used in the study. The average body weight of the rats was from about 180 to about 200 grams.

To induce arthritis, each rat was immunized with 200 μg of bovine type II collagen (4 mg/ml stocked in 10 mM acetic acid, commercially available from Elastin Products, Owensville, USA) emulsified in Freund's incomplete adjuvant (commercially available from Sigma Chemical Co., USA) on day 0 and then again on day 7. Day 16 was the first day that arthritic symptoms were observed and was defined to be the onset of induced arthritis.

All the rats in the experimental study had free access to drinking water and food at all times during this study.

The rats were randomized into the following 4 study groups:

Group 1: 4 rats each received 100 μl of saline per paw (labeled "Saline Control in FIGS. 1-8)

Group 2: 4 rats each received 100 μl of free DSP per paw, wherein the concentration of DSP is 1 mg/ml (labeled "Free DSP_1 mg/ml" in FIGS. 1-8).

Group 3: 4 rats each received 100 μl of the sustained release composition 1 per paw, wherein the concentration of DSP is 1 mg/ml (labeled "TLC399_1 mg/mg in FIGS. 1-4 and "TLC399_I 4 mg/ml in FIGS. 5-8).

Group 4: 4 rats each received 100 μl of the sustained release composition 2 per paw, wherein the concentration of DSP is 1.4 mg/ml (labeled "TLC399_1.4 mg/mg in FIGS. 1-4 and "TLC399_II 1.4 mg/ml in FIGS. 5-8).

The control or the DSP formulation was administered to both hind paws of the rat as a once only IA injection on day 19. The DSP dose administered to each paw is summarized in Table 2.

TABLE 2

The characteristics of the sustained release compositions

| Group Number | Dose volume (μl/paw) | Total No. of paw (No. of rats) | DSP Conc. (mg/mL) | Free DSP (mg/ml), based on encapsulated efficiency % |
|---|---|---|---|---|
| Group 1 (Saline) | 100 | 8 (4) | 0 | 0 |
| Group 2 (Free DSP in Saline) | 100 | 8 (4) | 1 | 1 |
| Group 3 (Sustained Release Composition 1) | 100 | 8 (4) | 1 | 0.685 |
| Group 4 (Sustained Release Composition 2) | 100 | 8 (4) | 1.4 | 0.959 |

During the 14-day study period, the rats were examined 3 times a week for the following outcomes:

Body weight loss, which is one of the parameters for evaluating the severity of arthritis.

Clinical Visual Arthritis Score, which is a visual score which correlates with the severity of arthritis. It was graded using an articular index of each paw, ranging from 0 to 4 (0=no edema or erythema on the foot pad; 1=slight edema and erythema on the foot pad; 2=mild edema and erythema on the foot pad; 3=moderate edema and erythema on the entire foot pad and the ankle; 4=severe edema and joint rigidity of the ankle, foot and digits). The Clinical Visual Arthritis Score for each rat was the sum of the articular index of both hind paws, with a maximum score of 8.

Hind paw volume and swelling. The hind paw volume was measured by UGO Plethysmometer 7149 measuring system. The final volume data was normalized with the average body weight (ml/kg) and edema was defined as the increase in paw volume on the day of measurement relative to day 0.

Results:

FIG. 1 shows the body weight changes in the 4 groups of rats. Body weight loss was observed on day 16 in all 4 groups of rats, which coincided with the onset of arthritis. The body weight loss continued from day 16 to day 19.

After the IA injection on day 19, a more pronounced weight loss was observed in the sustained release composition 1 and sustained release composition 2 groups, compared to the saline and free DSP groups. The weight loss could be caused by the loss of appetite, a known side effect of steroid. As the DSP was released from the sustained release compositions at a slower rate, the side effect of the steroid (loss of appetite) lasted longer. Hence, a more noticeable weight loss was observed in the groups receiving sustained release compositions.

Figure 2:
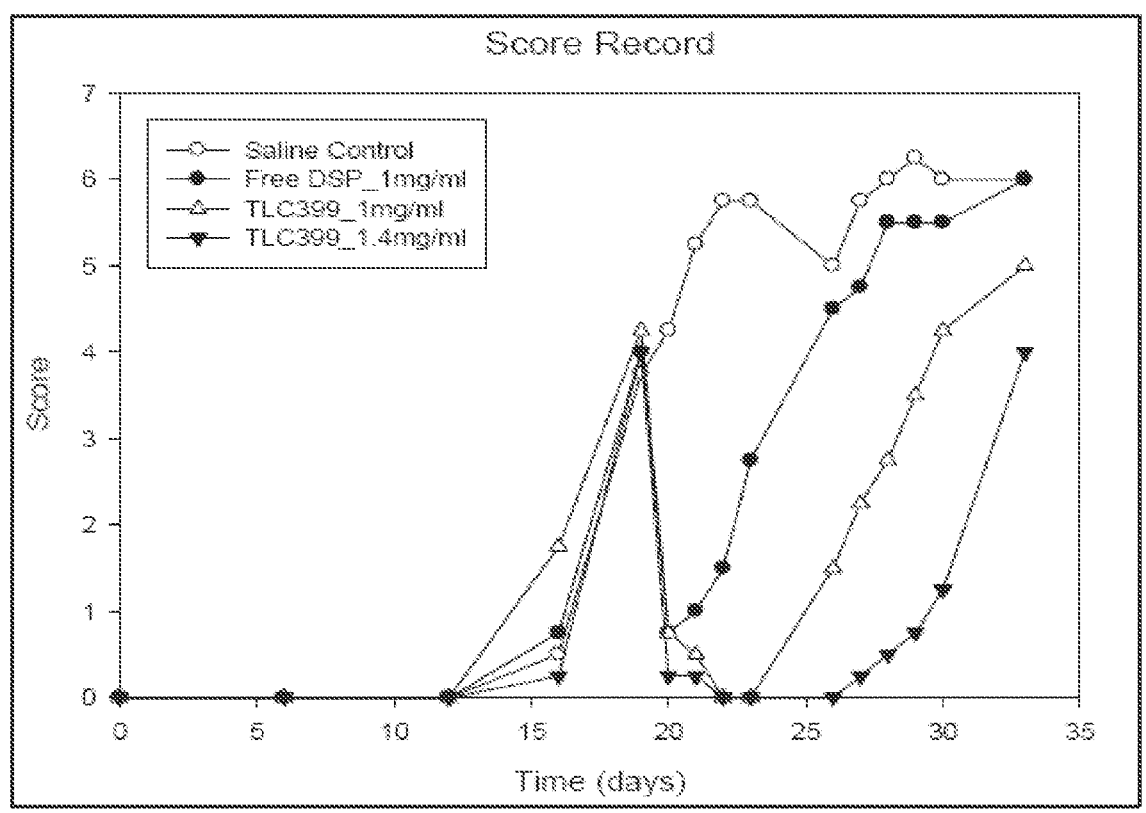
FIG. 2 is a line plot showing the changes in clinical visual arthritis score in 4 groups of rats after each group was subjected, respectively, to a single IA injection of saline, free DSP or the sustained release compositions.

FIG. 2 shows the change in clinical visual arthritis score in 4 groups of rats. Prior to the IA injection, the average score was 3.75 for the saline group, 4.0 for the free DSP and the sustained release composition 2 groups, and 4.25 for the sustained release composition 1 group.

24 Hours after the IA injection, the score dropped below 1 for all of the groups, except the saline group.

For the free DSP group, the score increased slowly 48 hours after the IA injection. The arthritis symptoms became more severe and the score reached 4.5 on day 26.

The rats in the sustained release composition 1 and sustained release composition 2 groups showed no arthritis symptoms for the following 4 days, with a score of 0 on days 23 and 24. On day 26, three rats in the sustained release composition 1 developed mild arthritis symptoms with an average score of 1.5, whereas no rat in the sustained release composition 2 group had any relapse symptoms, with the score remaining at 0. The rats in the free DSP group on day 26 had severe arthritis symptoms and a score of 4.5. On day 30, the rats in the sustained release composition 1 group developed severe arthritis, with a score above 4, whereas the rats in the sustained release composition 2 group had mild arthritis with a score of 1.5.

Figure 3:
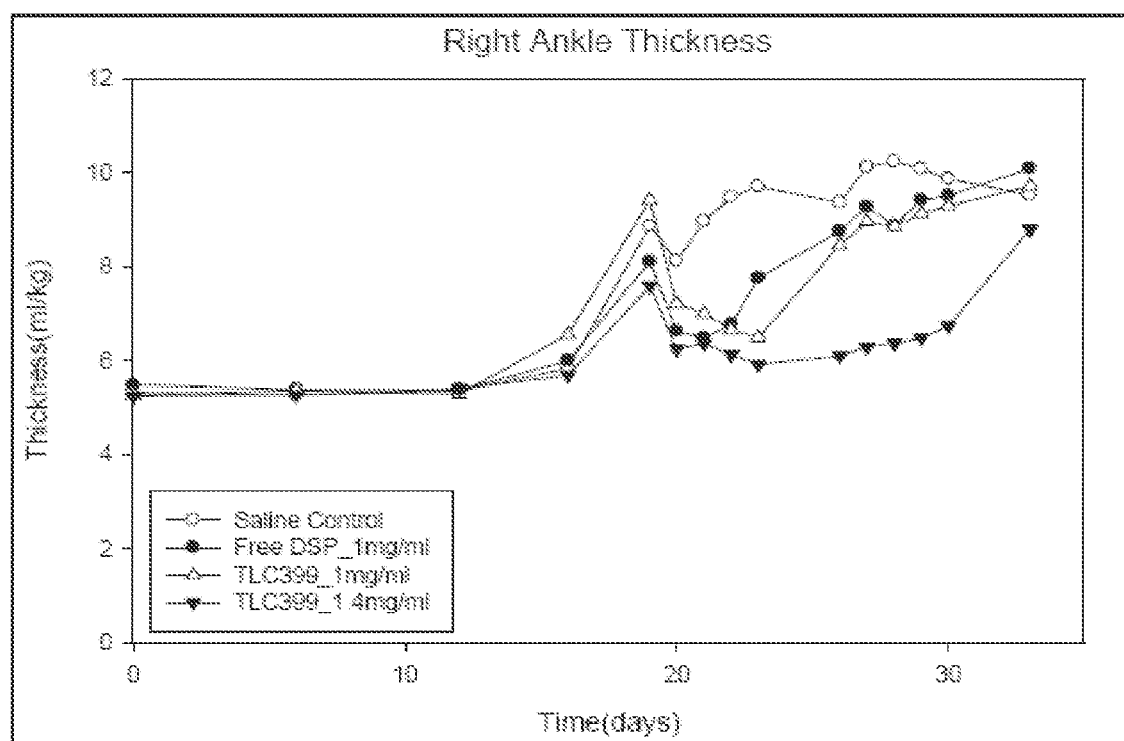
FIG. 3 is a line plot showing the changes in right ankle volume in 4 groups of rats after each group was subjected, respectively, to a single IA injection of saline, free DSP or the sustained release compositions.
Figure 4:
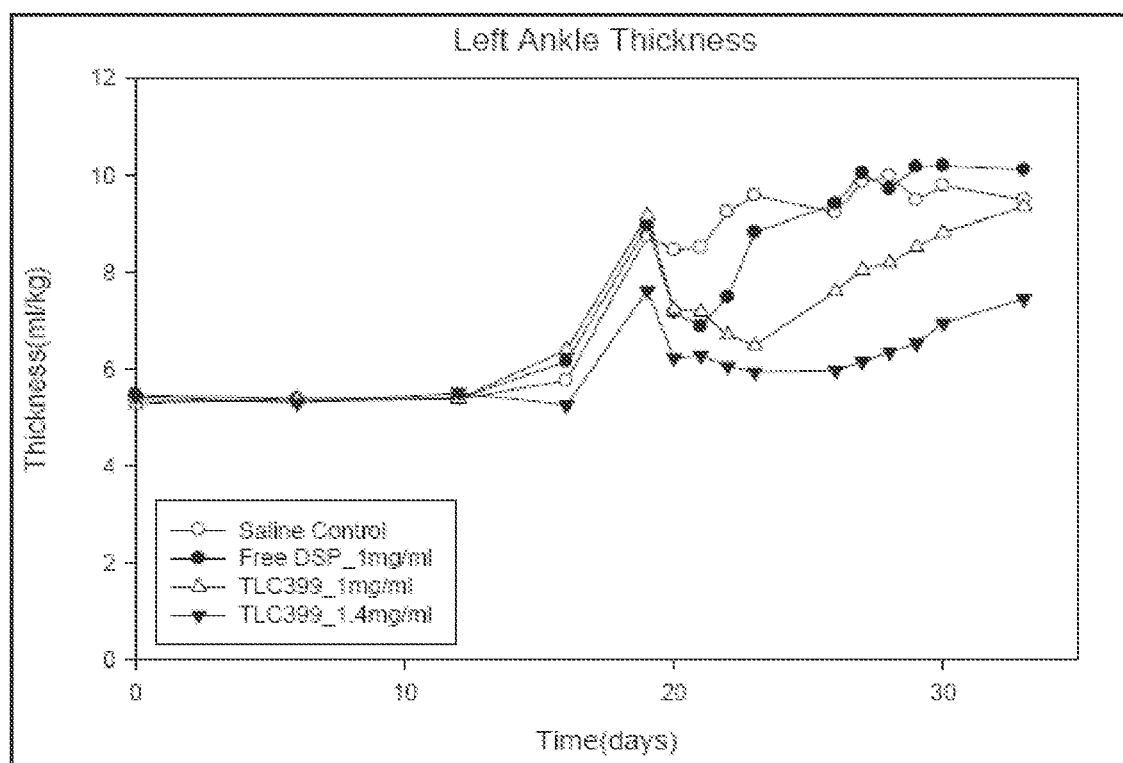
FIG. 4 is a line plot showing the changes in the left ankle volume in 4 groups of rats after each group was subjected, respectively, to a single IA injection of saline, free DSP or the sustained release compositions.

Referring to FIG. 3 and FIG. 4, after the IA injection on day 19, paw swelling volume decreased in all 4 groups on day 20. The temporary reduction of paw swelling volume in the saline group may have been due to the dilution of inflammatory factors by saline in the joint.

For the free DSP group, the effect of the IA injection lasted for 3 days. On day 23, both paws were swollen again, with the thickness around 7.5 ml/kg.

For the sustained release composition 1 group, paw swelling reduced significantly for the next 4 days. Both paws became swollen again on day 25, with an estimated thickness around 7.5 ml/kg.

For the sustained release composition 2 group, paw swelling reduced significantly for the next 10 days. Both paws became swollen again around day 34, and the thickness was above 8 ml/kg for the right ankle and 7.5 ml/kg for the left ankle.

The study described above supported a conclusion that a single IA injection of the sustained release composition was more effective in treating arthritis in experimental animals, as compared to free DSP.

Example 4: Multiple Injections of Sustained Release Composition for Treating Arthritis The design of this study is substantially similar to that of the study described in Example 3, except (a) there was no saline control group; and (b) study medication was administered by IA injection once a day for 4 days (day 26 to day 29).

Figure 5:
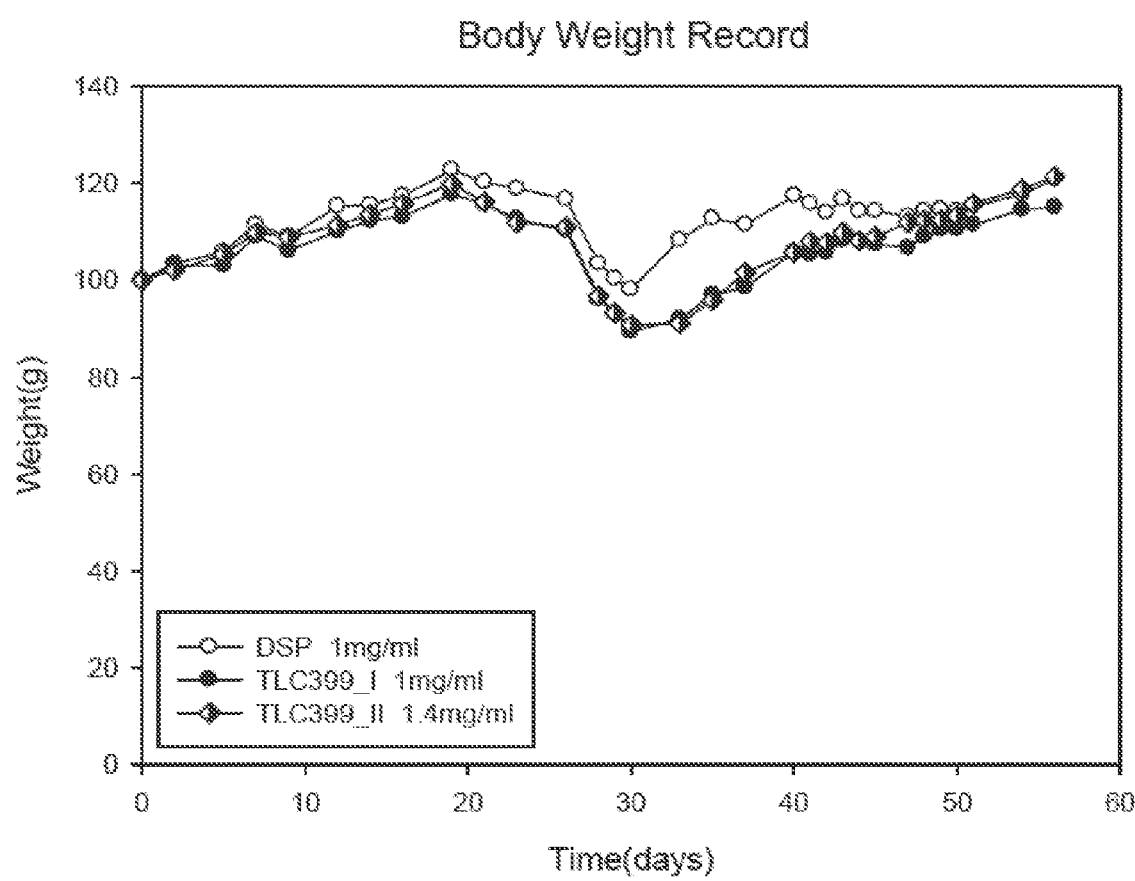
FIG. 5 is a line plot showing the changes in body weight in 3 groups of rats after four daily IA injections of free DSP or the sustained release compositions.

Results:

FIG. 5 shows the change in body weight in the 3 groups of rats (free DSP group, sustained release composition 1 group and sustained release composition 2 group). Body weight loss was observed on day 24 in all 3 groups of rats, which coincided with the onset of arthritis.

After the IA injections from day 26 to day 29, a more pronounced weight loss was observed in the 3 groups. As discussed in Example 3, the weight loss could be caused by the loss of appetite, a known side effect of steroid.

Figure 6:
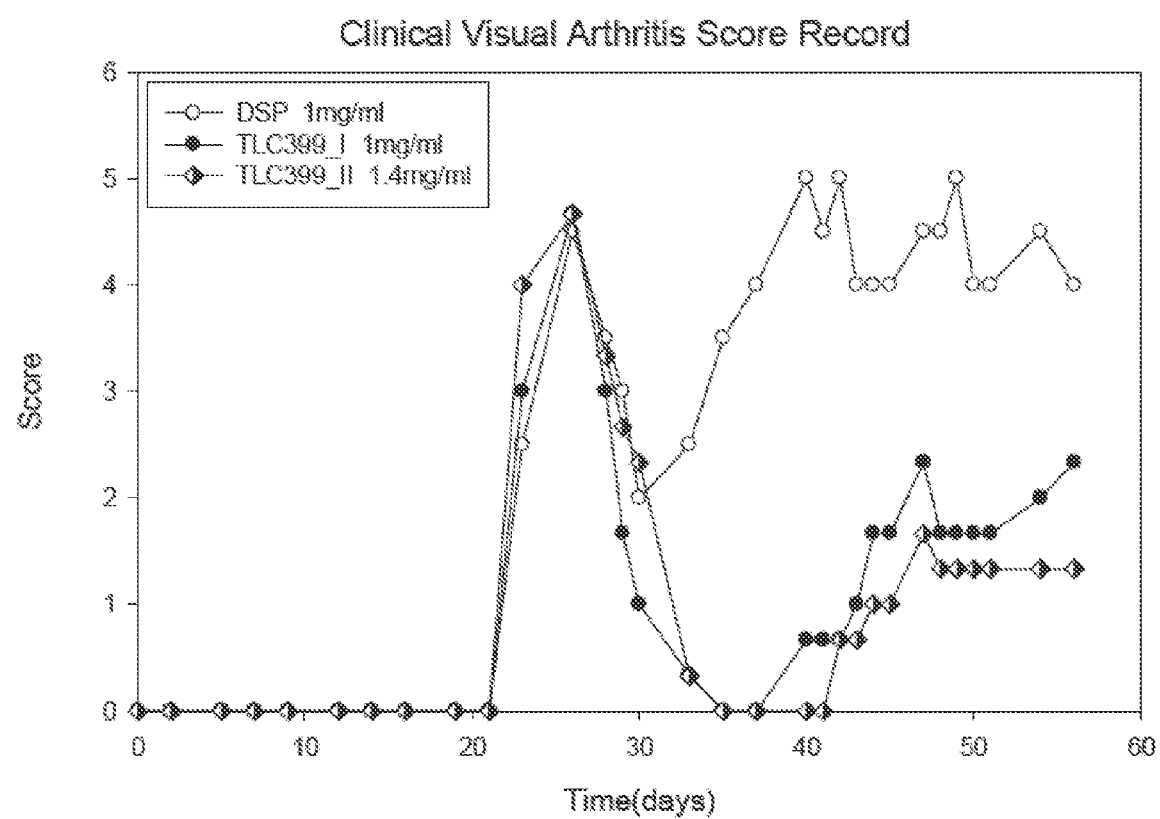
FIG. 6 is a line plot showing the changes in clinical visual arthritis score in 3 groups of rats after each group was subjected, respectively, to four daily IA injections of free DSP or the sustained release compositions.

FIG. 6 shows the change in clinical visual arthritis score in the 3 groups of rats. Prior to the IA injections, the average score was around 4.5 to 4.7.

For the free DSP group, the score dropped to 3 on day 30, the lowest recorded score in this study. The arthritis signs soon relapsed and became severe on day 33.

For the sustained release composition 1 and sustained release composition 2 groups, the arthritis score continued to decline after the treatment ended on day 29 and remained at zero (0) until day 37. In the sustained release composition 1 group, the rats first showed signs of relapse on day 40, whereas in the sustained release composition 2 group, the rats first showed signs of relapse on day 42.

Figure 7:
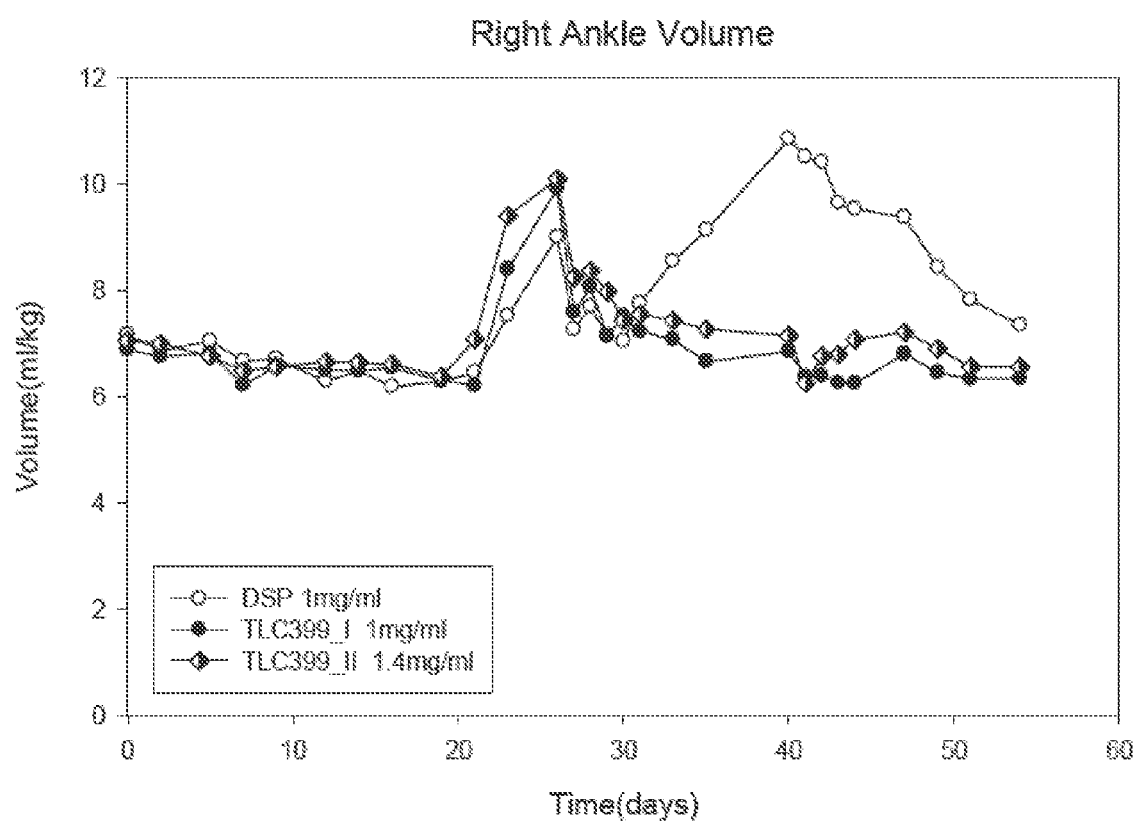
FIG. 7 is a line plot showing the changes in right ankle volume in 3 groups of rats after each group was subjected, respectively, to four daily IA injections of free DSP or the sustained release compositions.
Figure 8:
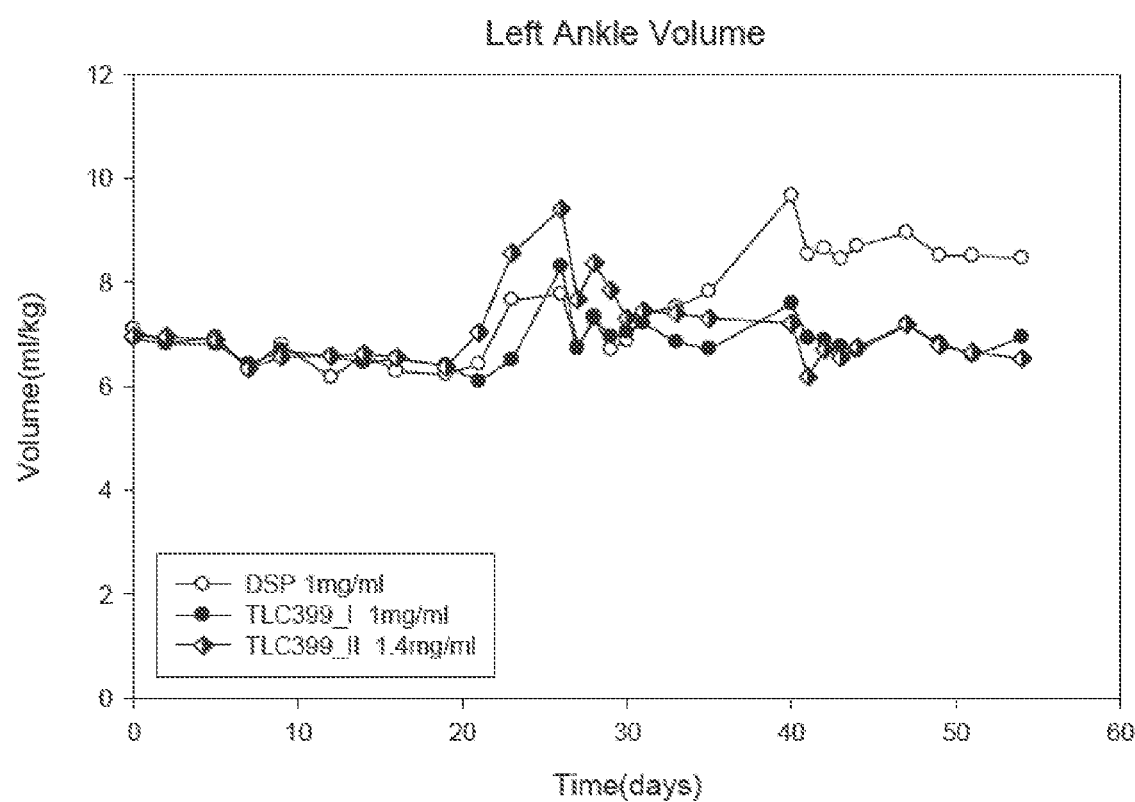
FIG. 8 is a line plot showing the changes in the left ankle volume in 3 groups of rats after each group was subjected, respectively, to four daily IA injections of free DSP or the sustained release compositions.

Referring to FIG. 7 and FIG. 8, paw swelling volume decreased in both paws across the 3 groups after 4 daily IA injections. For the free DSP group, the effect of the IA injection lasted for 1-2 days. On day 31, both paws were swollen again, reaching the peak on day 40.

For the sustained release composition groups, paw swelling reduced significantly for the next 14 days. In the sustained release composition 1 group, the first sign of paw swelling was noted on day 40 whereas in the sustained release composition 2 group, the first sign of paw swelling was noted on day 42.

The study described above supported a conclusion that 4 daily IA sustained release DPS injections were effective for treating arthritis in the experimental animals.

Example 5: Indomethacin Sustained Release Composition

Indomethacin sodium (Hubei Heng Lu Yuan Technology Co., Ltd, Hubei, China) was dissolved with saline to a final concentration of 5 mg/ml. The lyophilized liposome mixture described in Example 1 was reconstituted with 0.3 ml of indomethacin solution, resulting in indomethacin sustained release composition of reconstituted volume of 0.3 ml per vial, with the final concentrations of 5 mg/ml INN, 71 mg/ml DOPC, 8 mg/ml DOPG, 13 mg/ml cholesterol and 50 mg/ml mannitol.

Example 6: Collagen-Induced Arthritis Animal Model Used in the Experimental Study of Indomethacin Sustained Release Composition An in vivo evaluation of the effect of the indomethacin sustained release composition on arthritis was performed using 18 female Lewis rats (BioLASCO Taiwan Co, Ltd., Taiwan). The study design and the induction of arthritis in rats were substantially similar to that of the study in Example 3.

Figure 9:
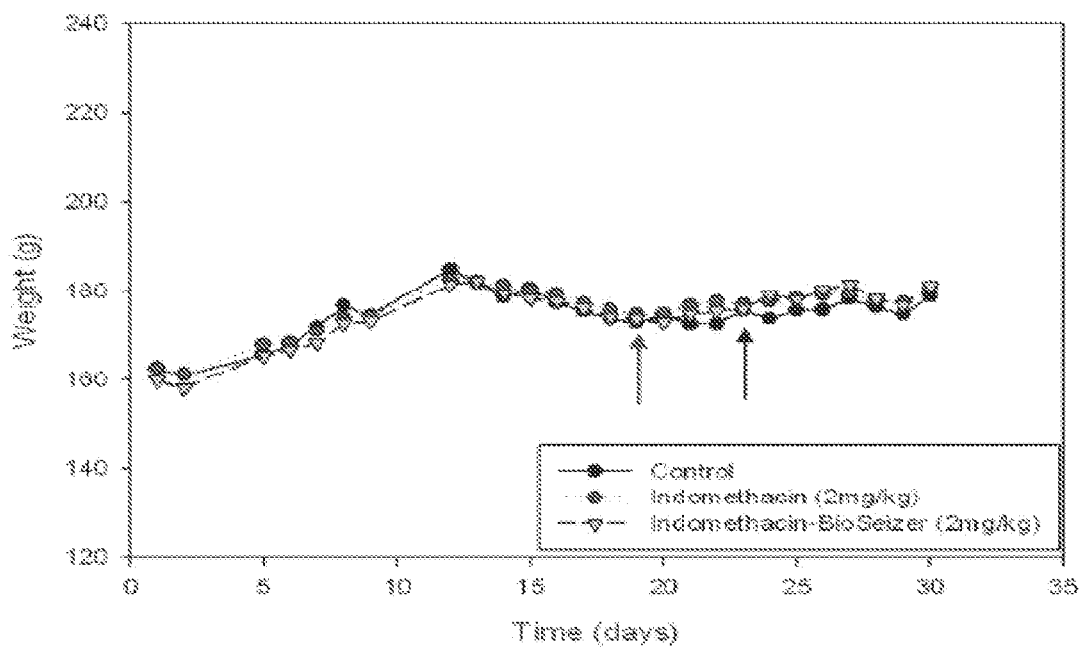
FIG. 9 is a line plot showing the changes in weight (panel a) and clinical arthritis score (panel b) of the three groups of rats after five daily IA injections of free indomethacin or indomethacin sustained release composition. The first arrow on day 19 indicates the first daily IA administration of indomethacin and the second arrow on day 23 indicates the last daily IA administration of indomethacin.
Figure 9:
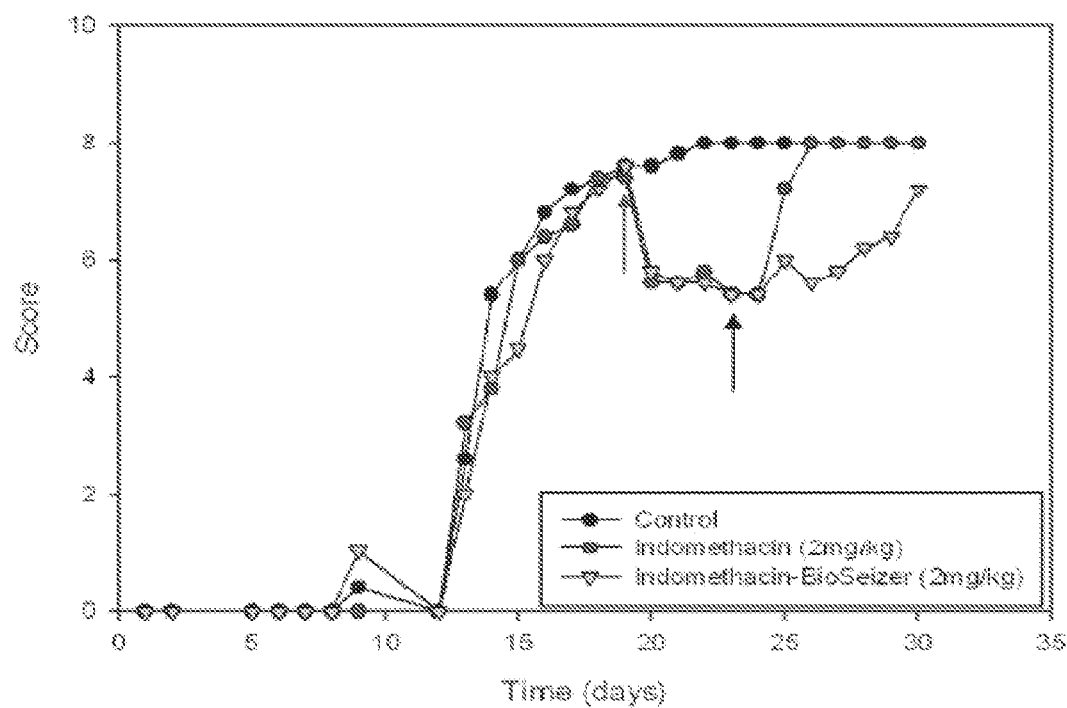

The arthritis treatments were initiated at the peak of the clinical visual arthritis score, which occurred at day 19. Eighteen rats were randomly divided into three groups (6 rats in each group): (1) control group (without any treatment, labeled "Control" in FIG. 9); (2) free indomethacin group (2 mg/kg indomethacin per dose, labeled "Indomethacin (2 mg/kg) in FIG. 9); and (3) indomethacin sustained release composition group (2 mg/kg indomethacin per dose; labeled "Indomethacin-BioSeizer (2 mg/kg) in FIG. 9). The rats in each group were given no treatment (control group), daily subcutaneous injection around the arthritis joints of free indomethacin or indomethacin sustained release composition, from day 19 to day 23. The dose of indomethacin in the administered compositions is listed in Table 4.

Table 4. The dose of free indomethacin solution and indomethacin sustained release composition.

TABLE 4

| Item | Indomethacin Sodium Conc. | Free Indomethacin Sodium Conc. |
| --- | --- | --- |
| Free Indomethacin Solution | 5 mg/ml | 5 mg/ml |
| Indomethacin sustained release composition | 4.65 mg/ml | 3.36 mg/ml |

The rats in this study gained body weight from the beginning of the study, and reached the peak on day 12. Body weight decreased in all three rat groups, as the signs of arthritis developed. Arthritis score reached its maximum on day 18, with the average arthritis score between 7.2-7.4, as illustrated in FIG. 9b.

From days 19 to 23, the arthritis symptoms were reduced in groups 2 and 3. In group 2 (free indomethacin group), the average arthritis score dropped from 7.4 to 5, with improved motor function and increased knee joint flexibility on day 20. On day 25, 2 days after the termination of the indomethacin treatment, signs of arthritis (such as stiff, swollen and erythematous joints) relapsed and the arthritis score reached 8.

In group 3 (indomethacin sustained release composition group), the average arthritis score decreased from 7.6 to 5.8 on day 20. The arthritis score remained under 7 until day 29 with prolonged treatment efficacy after the termination of treatment. The arthritis symptoms of group 3 became severe on day 30.

In summary, during the 5-day treatment of free indomethacin (group 2) or indomethacin sustained release compositions (group 3), arthritis symptoms were significantly ameliorated in both groups. Arthritis signs returned two days after the withdrawal of free indomethacin in group 2, whereas in group 3, the amelioration of arthritis signs continued for 6 days after termination of the treatment. The results of the study summarized above support a conclusion that the indomethacin sustained release composition maintains the efficacy of indomethacin in the joint for a longer period of time than free indomethacin.

Example 7: Etanercept Sustained Release Composition

Lyophilized liposome mixture described in Example 1 was reconstituted with 0.3 ml of Enbrel (50 mg/ml of etanercept, commercially available from Wyeth Pharmaceuticals, Inc., Collegeville, USA), resulting in an etanercept sustained release composition with reconstituted volume of 0.3 ml per vial. The final concentration of lipid and etanercept in the etanercept sustained release composition is: 42.8 mg/ml etanercept, 70.7 mg/ml DOPC, 8 mg/ml DOPG, 13 mg/ml cholesterol and 50 mg/ml mannitol.

Example 8: Collagen-Induced Arthritis Animal Model Used in the Experimental Study of Etanercept Sustained Release Composition An in vivo evaluation of the effect of the etanercept sustained release composition on arthritis was performed using 18 female Lewis rats (BioLASCO Taiwan Co, Ltd., Taiwan). The study design and the induction of arthritis in rats were substantially similar to that of the study in Example 3, except bovine type II collagen was administered on day 0, day 7 and day 17.

The arthritis treatments were initiated at the peak of the clinical visual arthritis score, which occurred at day 23. Eighteen rats were randomly divided into three groups (6 rats in each group): (1) control group (without any treatment, labeled "Control" in FIG. 10); (2) free etanercept group (50 mg/kg etanercept per dose, labeled "Enbrel (50 mg/kg) in FIG. 10); and (3) etanercept sustained release composition group (50 mg/kg etanercept per dose; labeled "Enbrel-BioSeizer (50 mg/kg) in FIG. 10). The rats in each group received no treatment or two subcutaneous injections around the arthritic joints of free etanercept or etanercept sustained release composition, on day 23 and day 26. The dose of etanercept in the administered compositions is listed in Table 5.

Table 5. The dose of free etanercept solution and etanercept sustained release composition.

TABLE 5

| Item | Etanercept Conc. | Free Etanercept Conc. |
| --- | --- | --- |
| Free Etanercept Solution | 50 mg/ml | 50 mg/ml |
| Etanercept sustained release composition | 42.8 mg/ml | 40.3 mg/ml |

Figure 10:
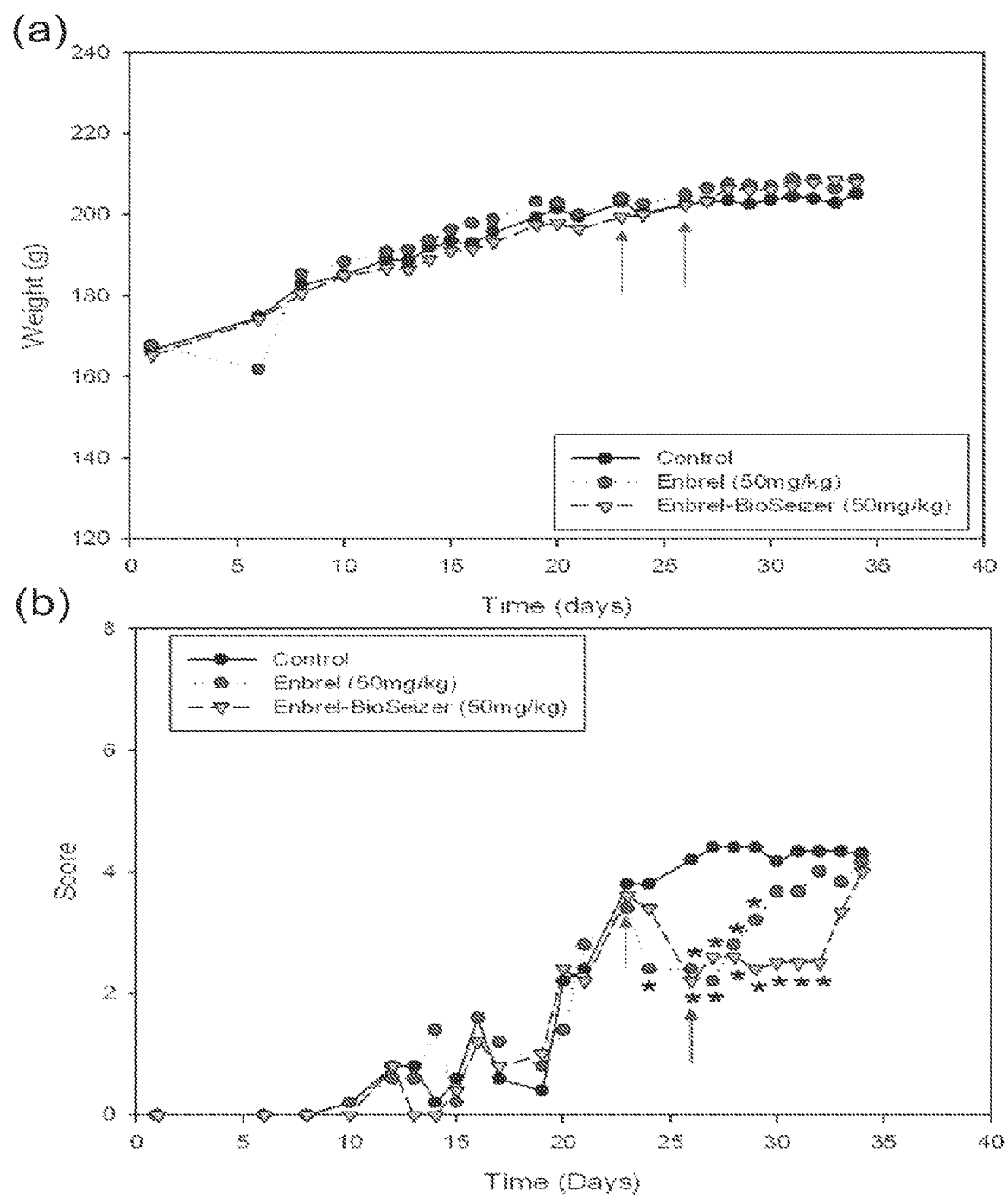
FIG. 10 is a line plot showing the changes in weight (panel a) and clinical arthritis score (panel b) of the three groups of rats after two IA injections of free etanercept or etanercept sustained release composition. The first arrow on day 23 indicates the first IA administrations of etanercept, and the second arrow on day 26 indicates the second IA administration of etanercept.

The rats in this study developed signs of arthritis soon after type II collagen immunization and reached the peak on day 23, with the average arthritis score between 3.6 to 3.8, as illustrated in FIG. 10.

During the treatment period (day 23 to 26), the signs of arthritis were reduced in the treatment groups (groups 2 and 3). In group 2 (free etanercept group), the average arthritis score dropped to 2.4 on day 26 but arthritis relapsed 3 days after the termination of the free etanercept. On day 30, the arthritis score reached 4 and the rats became immobile due to joint swelling and stiffness.

In group 3 (etanercept sustained release composition group), the average arthritis score decreased to 2.2 on day 26 and remained under 2.5 until day 32. The arthritis symptoms of group 3 became severe again on day 33.

In summary, during the 4-day treatment of free etanercept (group 2) or etanercept sustained release compositions (group 3), arthritis symptoms were significantly ameliorated in both groups. Arthritis signs returned three days after the withdrawal of free etanercept in group 2 whereas in group 3, the amelioration of arthritis signs continued for 5 days after the termination of the treatment. The results of the experimental study summarized above support a conclusion that the etanercept sustained release composition maintains the efficacy of etanercept in the joint for a longer period of time than free etanercept.

Example 9: Methotrexate Sustained Release Composition

The lyophilized liposome mixture described in Example 1 was reconstituted with 0.3 ml of methotrexate sodium (Pharmachemie BV, Inc.), resulting in a methotrexate sustained release composition with a reconstituted volume of 0.3 ml per vial. The final concentration of lipid and methotrexate in the methotrexate sustained release composition is: 2.5 mg/ml methotrexate, 70.7 mg/ml DOPC, 8 mg/ml DOPG, 13 mg/ml cholesterol and 50 mg/ml mannitol.

Example 10: Collagen-Induced Arthritis Animal Model Used in the Experimental Study of Methotrexate Sustained Release Composition An in vivo evaluation of the effect of the methotrexate sustained release composition on arthritis was performed using 18 female Lewis rats (BioLASCO Taiwan Co, Ltd., Taiwan). The study design and the induction of arthritis in rats were substantially similar to that of the study in Example 3, except bovine type II collagen was administered on day 0, day 7 and day 17.

The arthritis treatments were initiated at the peak of the clinical visual arthritis score, which occurred at day 23. Eighteen rats were randomly divided into three groups (6 rats in each group): (1) control group (without any treatment, labeled "Control" in FIG. 11a); (2) free methotrexate group (1 mg/kg methotrexate per dose, labeled "Methotrexate (1 mg/kg) in FIG. 11a); and (3) methotrexate sustained release composition group (1 mg/kg methotrexate per dose; labeled "Methotrexate-BioSeizer (1 mg/kg) in FIG. 11a). The rats in each group were given no treatment (control group) or two subcutaneous injections around the arthritic joints of either free methotrexate or methotrexate sustained release composition, on day 23 and day 26. The dose of methotrexate in the administered compositions is listed in Table 6.

Table 6. The dose of free methotrexate solution and methotrexate sustained release composition.

TABLE 6

| Item | Methotrexate Sodium Conc. | Free Methotrexate sodium Conc. |
|---|---|---|
| Free Methotrexate Solution | 2.5 mg/ml | 2.5 mg/ml |
| Methotrexate sustained release composition | 2.3 mg/ml | 1.8 mg/ml |

Figure 11:
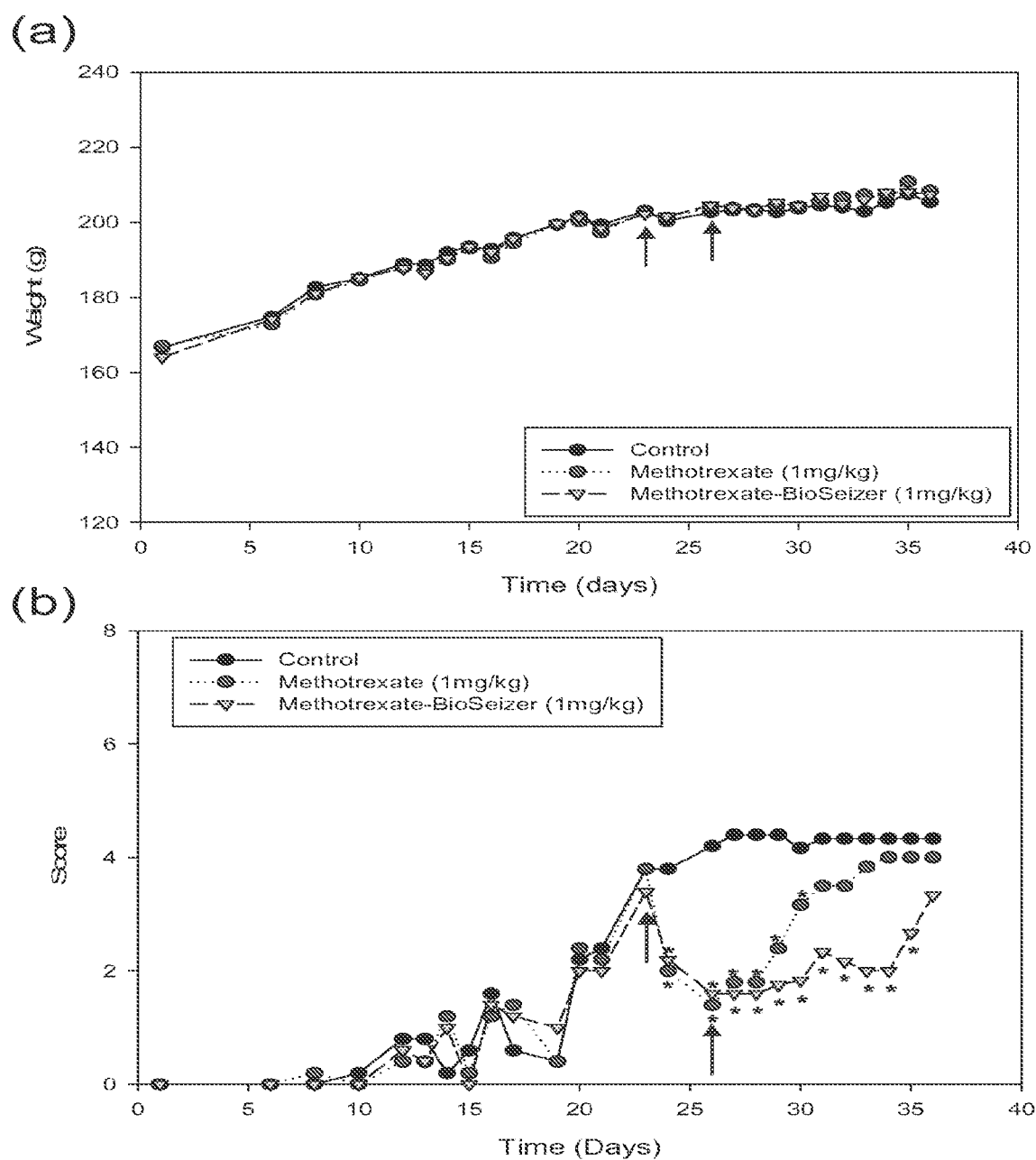
FIG. 11 is a line plot showing the changes in weight (panel a) and clinical arthritis score (panel b) of the three groups of rats after two IA injections of free methotrexate or methotrexate sustained release composition. The first arrow on day 23 indicates the first IA administration of methotrexate and the second arrow on day 26 indicates the second IA administration of methotrexate.

The rats in this study developed signs of arthritis soon after type II collagen immunization and reached the peak on day 23, with the average arthritis score between 3.4 to 3.8, as illustrated in FIG. 11b.

From days 23 to 26, the arthritis symptoms were reduced in groups 2 and 3. In group 2 (free methotrexate group), the average arthritis score dropped from 3.7 to 1.4 on day 26. On day 30, 4 days after the termination of methotrexate treatment, the rats became hypoactive and the arthritis score reached 3.5.

In group 3 (methotrexate sustained release composition group), the average arthritis score decreased from 3.4 to 1.6 on day 26. The arthritis score remained around 2 until day 35, and increased after that.

In summary, methotrexate treatment ameliorated arthritis symptoms in group 2 and 3. Arthritis signs returned 4 days after the withdrawal of free methotrexate in group 2, whereas in group 3, the amelioration of arthritis signs continued for 9 days after the termination of the treatment. The results of the experimental study summarized above support a conclusion that the methotrexate sustained release composition maintains the efficacy of methotrexate in the joint for a longer period of time than free methotrexate.

Different arrangements and combinations of the elements and the features described herein are possible. Similarly, some features and subcombinations are useful and may be employed without reference to other features and subcombinations. For example, if a method is disclosed and discussed and a number of modifications that can be made to a composition included in the method are discussed, each and every combination and permutation of the method, and the modifications that are possible are specifically contemplated unless specifically indicated to the contrary. Likewise, any subset or combination of these is also specifically contemplated and disclosed. Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the present invention.

What is claimed is:

1. A mixture for intraarticular delivery of a therapeutic agent, the mixture comprising:
   a first phospholipid, a second phospholipid, and cholesterol, wherein the first phospholipid is selected from the group consisting of 1,2-dioleoyl-sn-glycero-3-phosphatidylcholine (DOPC), 1-palmitoyl-2-oleoyl-sn-glycero-3-phosphatidylcholine (POPC), soy phosphatidylcholine (SPC), and egg phosphatidylcholine (EPC), and the second phospholipid is polyethyleneglycol distearoylphosphatidylethanolamine (PEG-DSPE) or dipalmitoylphosphatidylglycerol (DOPG); and
   wherein the cholesterol is at a mole percent of about 10 to about 33 based on the total amount of the first phospholipid, the second phospholipid and cholesterol.

2. The mixture of claim 1, wherein the second phospholipid is DOPG at a mole percent ratio about 3 to 37.5 based on the total amount of the first phospholipid, the second phospholipid and cholesterol.

3. The mixture of claim 1, wherein the first phospholipid is DOPC and the second phospholipid is DOPG.

4. The mixture of claim 3, wherein the mole percent of DOPC:DOPG:cholesterol of the liposome is about 29.5 to 90:3 to 37.5:10 to 33.

5. The mixture of claim 3, wherein the mole percent of DOPC:DOPG:cholesterol of the liposome is about 56.25 to 72.5:7.5 to 18.75:20 to 25.

6. A method for delivering a therapeutic agent by the mixture of claim 4 to a subject suffering from arthritis, which comprises
   providing a composition comprising:
      the mixture of claim 1 and the therapeutic agent; and
      intraarticularly administrating the composition to a subject suffering from arthritis.

7. The method of claim 6, wherein the therapeutic agent comprises a water soluble steroid solution comprising an effective amount of a water soluble steroid or a pharmaceutically acceptable salt thereof.

8. The method of claim 7, wherein the water soluble steroid is dexamethasone sodium phosphate.

9. The method of claim 7, wherein the water soluble steroid solution has a potency equivalent to about a 2 mg dose to about a 8 mg dose of dexamethasone.

10. The method of claim 6, wherein the therapeutic agent comprises a nonsteroidal anti-inflammatory drug or a pharmaceutically acceptable salt thereof.

11. The method of claim 10, wherein the nonsteroidal anti-inflammatory drug is indomethacin.

12. The method of claim 10, wherein the pharmaceutically acceptable salt of the nonsteroidal anti-inflammatory drug is indomethacin sodium.

13. The method of claim 10, wherein the dose of the nonsteroidal anti-inflammatory drug or its pharmaceutically acceptable salt is 4.65 to 5 mg/ml.

14. The method of claim 6, wherein the therapeutic agent comprises a disease-modifying anti-rheumatic drug (DMARD).

15. The method of claim 14, wherein the DMARD comprises a TNF-α antagonist.

16. The method of claim 15, wherein the TNF-α antagonist is etanercept.

17. The method of claim 16, wherein the dose of etanercept is 42.8 mg/ml to 50 mg/ml.

18. The method of claim 15, wherein the TNF-α antagonist is adalimumab.

19. The method of claim 14, wherein the DMARD comprises methotrexate or a pharmaceutically acceptable salt thereof.

20. The method of claim 19, wherein the pharmaceutically acceptable salt of methotrexate is methotrexate sodium.

21. The method of claim 19, wherein the dose of methotrexate or its pharmaceutically acceptable salt is 2.3 to 2.5 mg/ml.

* * * * *